United States Patent [19]

Honard et al.

[11] Patent Number: 4,685,900

[45] Date of Patent: Aug. 11, 1987

[54] THERAPEUTIC DEVICE

[75] Inventors: Mark R. Honard, Mentor; Mark A. Holmes, Chardon; Robert D. Jarrett, Painesville, all of Ohio

[73] Assignee: BioSpecific Technologies, Inc., Painesville, Ohio

[21] Appl. No.: 809,857

[22] Filed: Dec. 18, 1985

Related U.S. Application Data

[63] Continuation-in-part of Ser. No. 499,989, Jun. 1, 1983, abandoned.

[51] Int. Cl.$^4$ ............................................. A61M 37/00
[52] U.S. Cl. ............................................. 604/5; 427/2
[58] Field of Search ........................... 427/2; 604/4–6, 604/406, 416; 210/321.2

[56] References Cited

U.S. PATENT DOCUMENTS

| | | | |
|---|---|---|---|
| Re. 31,712 | 10/1984 | Giese | 427/2 |
| 2,715,097 | 8/1955 | Guarino | 604/5 |
| 3,489,647 | 1/1970 | Kolobow | 604/5 |
| 3,794,584 | 2/1974 | Kunin | 604/4 |
| 3,826,678 | 7/1974 | Hoffman | 604/5 |
| 3,848,580 | 10/1974 | Hyden et al. | |
| 3,864,259 | 2/1975 | Newhart | 604/5 |
| 3,959,128 | 5/1976 | Harris | 604/5 |
| 3,963,613 | 6/1976 | Chibata et al. | 604/5 |
| 4,059,685 | 10/1977 | Johnson | |
| 4,061,141 | 12/1977 | Hyden et al. | |
| 4,182,750 | 1/1980 | Sullivan et al. | 604/5 |
| 4,215,688 | 8/1980 | Terman et al. | 128/214 R |
| 4,222,907 | 9/1981 | Katz et al. | 260/6 |
| 4,357,311 | 10/1982 | Schutt | |
| 4,361,484 | 11/1982 | Larsson et al. | 210/632 |
| 4,362,155 | 12/1982 | Skurkovich | 604/6 |
| 4,375,407 | 3/1983 | Kronick | 209/8 |
| 4,381,004 | 4/1983 | Babb | |
| 4,430,229 | 2/1984 | Yamawaki et al. | |
| 4,551,435 | 11/1985 | Liberti et al. | |

FOREIGN PATENT DOCUMENTS

| | | |
|---|---|---|
| 054249 | 6/1982 | European Pat. Off. |
| 054799 | 6/1982 | European Pat. Off. |
| 0082345 | 6/1983 | European Pat. Off. |
| 3109123 | 9/1982 | Fed. Rep. of Germany |
| 2178085 | 11/1973 | France |

OTHER PUBLICATIONS

Review of Physiological Chemistry, 16th Edition, Harold A. Harper, Ph.D., Lange Medical Publications, p. 167.

Textbook of Immunology, James T. Barrett, Ph.D, The C. V. Mosby Company, 1970, p. 21.

Hoffman et al, "New Approaches to Non-Thrombogenic Materials", Coagulation: Curr. Res. Clin. Appl., Proc. Symp., 1972, pp. 201–226.

Hoffman et al, "Covalent Binding of Biomolecules to Radiation Grafted Hydrogels on Inert Polymer Surfaces", Trans., Am. Soc. Artif. Intern. Organs, 1972, vol. 8, pp. 10–13.

Ratner et al, "Synthetic Hydrogels for Biomedical Applications", ASC Symp. Ser., 1976, vol. 31, pp. 1–36.

McCullough et al, "Therapeutic Plasma Exchange", Lab. Med 12(12), p. 745 (1981).

Terman et al, "Extracorporeal Immunoadsorption: Initial Experience in Human Systemic Lupus Erythematosus", The Lancet, Oct. 20, 1979, pp. 824–826.

Terman et al, "Specific Removal of Circulated Antigen by Means of Immunoadsorption", Febs Letters, vol. 61, No. 1, Jan. 1976, pp. 59–62.

Bansal et al, "Ex Vivo Removal of Serum IgG in a Patient with Colon Carcinoma", Cancer, 42(1), pp. 1–18 (1978).

Malchesky et al, "On-Line Separation of Macromolecules by Membrane Filtration with Cryogelation". Artif. Organs, 4:205 (1980).

A. S. Hoffman, "Use of Radiation Technology in Preparing Materials for Bioengineering and Medical Science", Ind. Appl. Radiosat. Radiat. Technol., Proc. Int. Conf., 1982, pp. 279–321.

Primary Examiner—C. Fred Rosenbaum
Assistant Examiner—Gene B. Kartchner
Attorney, Agent, or Firm—Thoburn T. Dunlap; William A. Skinner

[57] ABSTRACT

A therapeutic device for removing pathological effectors brom body fluids of a patient is disclosed. Said device includes a chamber for receiving the body fluids and positioned within the chamber is a biospecific polymer. Said biospecific polymer interacts with and binds specific pathological effectors carried by the body fluid that is passed through the chamber.

19 Claims, 9 Drawing Figures

THERAPEUTIC DEVICE

This application is a continuation-in-part of application Ser. No. 499,989, filed June 1, 1983, now abandoned.

BACKGROUND OF THE INVENTION

The present invention relates to a device for the extracorporeal treatment of disease. The course of many disease states is often reflected by elevated levels of specific blood proteins. This phenomenon is typically utilized as a diagnostic tool to define the pathology and to follow the course of clinical treatment. In many instances, these specific blood proteins are directly or indirectly responsible for the primary and secondary manifestations of the disease process. "Autoimmune" diseases can be described as diseases characterized by circulating antibodies to endogenous substrates and tissue proteins required by the body for normal growth and maintenance. "Neoplastic" diseases are typically characterized by uncontrolled growth of an undifferentiated transformed cell line which evades or compromises the body's natural defense mechanisms by producing immunosupressant blocking factors, surface antigen masking components and/or growth regulator constituents. Specific compartmentalization of these pathological effectors (i.e., causative agent) onto a biocompatible substrate is consistent with the restoration of "normal" body function by removal of the pathological effectors of the disease process.

The basic function of the organs, cells and molecules that comprise the immune system is to recognize and to eliminate from the body foreign substances. These foreign substances are eliminated by reaction between the foreign substance and antibodies which are formed in response to the substance. In general, this function is performed efficiently and without detriment to the host. However, in certain instances, disturbances can occur which can lead to pathogenic disorders such as, for example, an uncontrolled response (allergic disorders) or an abnormal response (autoimmune disease). The pathogenesis of both of these disorders is related directly or indirectly to the production of antibodies with cross reactivities to either environmental antigens (allergens) or self-antigens.

An autoimmune disease is a pathological condition arising when a host responds immunologically by production of antibodies with reactivity to a self-antigen. Autoimmunity can affect almost every part of the body, and generally involves a reaction between a self-antigen and an immunoglobulin (IgM or IgG) antibody. Representative autoimmune diseases can involve the thyroid, kidney, pancreas, neurons, gastric mucosa, adrenals, skin, red cells and synovial membranes as well as thyroglobulin, insulin, deoxyribonucleic acids and immunoglobulins.

For some types of autoimmune and neoplastic diseases, non-specific immunosuppressant treatments, such as whole body X-irradiation or the administration of cytotoxic drugs, have been used with limited success. The disadvantages of such treatment include the toxicity of the agents used, and the increased incidence of various cancers, especially lymphomas and reticulum cell sarcomas, following such therapy. In addition, the use of non-specific agents for chronic cellular suppression greatly increases the susceptibility of the patient to serious infection from environmental fungi, bacteria and viruses which under ordinary circumstances would not cause problems. The invention disclosed herein is specific in that it removes only the pathological effector or those groups of pathological effectors which are related to and responsible for the manifestations of a particular disease.

In viewing the state of the art, one finds that most recently there have been generally two approaches to therapeutic treatments for autoimmune and/or neoplastic diseases. The first of these is to introduce a material into the patient which causes a specific type of immunological tolerance to be produced. This suppression of antibody response would then effect a tolerance to the offending antigen. A typical example of this type of approach is U.S. Pat. No. 4,222,907 issued to Katz on Sept. 16, 1981. In this reference, the diseased patient is given a therapeutic treatment which consists of introducing conjugates of an antigen linked to a D-glutamic acid: D-lysine copolymer.

The second approach has been the extracorporeal route. The procedures generally involve the removal of whole blood, separation of cellular and soluble blood substances, substitution or treatment of blood plasma and recombination-infusion of the treated whole blood. The first example of this approach would be plasma substitution or exchange with salt, sugar and/or protein solutions and is described by McCullough et al, "Therapeutic Plasma Exchange," Lab. Med. 12(12), p. 745 (1981). Plasma exchange is a rather crude technique that requires a large volume of replacement solution. A second example of this approach involves physical and/or biochemical modification of the plasma portion of whole blood. Typical of the state of the art of this therapeutic treatment are, for example, the Terman et al article "Extracorporeal Immunoadsorption: Initial Experience in Human Systemic Lupus Erythematosus," The Lancet, Oct. 20, 1979, pages 824–826. This article describes a hemodialysis type system utilizing two mechanical filters with a DNA collodian charcoal filter between said two mechanical filters. Typical of this state of the art, however, the adsorbent column is only semispecific for immune components because the charcoal substrate will nonspecifically delete many vital low molecular weight constituents from the treated plasma. A second application of this approach can be illustrated by the Terman et al article "Specific Removal of Circulated Antigen by Means of Immunoadsorption," FEBS Letters, Vol. 61, No. 1, Jan. 1976, pages 59–62. This reference teaches the specific removal of radiolabeled antigen by antibody treated cellulosic membranes. The author, however, demonstrates that control membranes have a significant capacity to non-specifically adsorb proteins. A third application of this approach is illustrated by the Bansal et al article "Ex vivo Removal of Serum IgG in a Patient With Colon Carcinoma," Cancer, 42(1), pp. 1–18 (1978). This report teaches the semispecific absorption of immunoglobulin by ex vivo treatment of plasma with formalin and heat-killed *Staphylococcus aureas*. The biological activity of certain strains of *S. aureas* is attributed to a molecule present on the cell wall, called Protein A, which interacts and binds with the Fc portion of mammalian IgG. This treatment, because it interacts with the Fc moiety, does not discriminate between normal and pathological IgG components and experiments have shown the possibility of significant side effects.

A fourth application of this approach can be illustrated by the Malchesky et al article "On-line Separation of Macromolecules by Membrane Filtration With Cryogelation," Artif. Organs 4:205, 1980. This publication teaches the semi-specific removal of cryoglobulin substances from plasma by the combination of filtration and cold treatment chambers. The incidence and composition of cryoglobular precipitates are not necessarily consistent with or indicative of many autoimmune or neoplastic diseases.

Another problem associated with the current state of the art is that without systems using mechanical filtration, the specific pathological effectors desired to be removed have not been removed in large enough amounts to do much good for the diseased patient in that the columns do not specifically adsorb substantially only the desired specific pathological effectors.

It has now been found that high specificity of pathological effector removal can be effectuated by treatment of body fluids in an economical and therapeutic procedure using the device of the present invention.

SUMMARY OF THE INVENTION

Broadly stated, this invention relates to a device for the extracorporeal treatment of disease comprising: means for withdrawing a body fluid from a patient, means for treating the body fluid including a chamber for receiving the body fluid and a biospecific polymer positioned within said chamber which will treat the body fluid by binding a specific pathological effector or specific group of pathological effectors carried by the body fluid that is passed through said chamber, and means for returning the body fluid to the patient.

The biospecific polymer contains a fixed capacity, affinity and specificity for selective adsorption of pathological effectors. The pathological effectors are compartmentalized, e.g., are adsorbed onto the biospecific polymer and are thus diverted away from their endogenous receptors. This chemisorptive process ultimately consumes the biospecific polymer, serving to control and eliminate disease states by removing elevated pathological immune, nutritional and hormonal constituents from the diseased body fluid. Degenerative and metabolic disorders are diminished or eliminated by removing a key effector from a pathological process.

As used herein and hereafter a biospecific polymer is a biocompatible polymer support which has a biological or biologicals attached to it which can specifically remove desired pathological effector or pathological effectors.

These and other objects of the present invention are disclosed and described in the detailed description below and in the appended claims.

DETAILED DESCRIPTION

I. Withdrawing Means

Withdrawing means is defined herein as being a means of providing access to the body fluid of interest of the patient to be treated. In the majority of instances, the body fluid to be treated will be the blood or plasma of a patient. Thus, the manner of access and the type of access hereinbelow described is for the most common body fluid, i.e., the patient's blood. However, it is to be understood that access to any of the body fluids of interest may be provided by using well-known techniques and procedures in the medical arts. The access method is not critical with the caveat that it provides the required body fluid for the patient's treatment. In the case of vascular access an indwelling large bore cannula may be used intravenously or arterially. Examples of suitable veins and arteries include the antecubital vein, subclavian vein and brachial or radial arteries. It is further understood that an arterial-venous shunt or fistulae may also be used. In this case, the heart provides the pressure differential for fluid movement. If an AV shunt fistulae is not used, the preferred means for providing the pressure differential for fluid movement by a venous access is a roller-peristaltic pump capable of providing a flow rate of about 30 ml per minute to about 200 ml per minute.

In cases where anticoagulants may be useful or necessary, suitable anticoagulants can be used utilizing well-known techniques and procedures in the medical arts. Suitable anticoagulants include, for example, acid citrate dextrose (approximately 1 ml to every 8 ml's of whole blood), heparin, heparin/acidic acid dextrose mixtures (e.g. 1250 IU heparin in 125 ml acid citrate dextrose/L), and prostaglandin. It is to be appreciated that in using anticoagulants such as heparin and prostaglandin it is generally understood that a counteracting medication could be administered to the treated blood or plasma before returning or giving said blood or plasma to a patient.

Further, in the case of treating plasma, it is understood that any conventional methods of removing the formed blood components may be used. Suitable examples of methods of separating plasma from formed blood components include, plasmapheresis, centrifugal cell separation, and cell sedimentation in a plasma bag. Where possible both continuous separation and intermittent (batch) separation are suitable—the aforementioned methods of separation are independent of the present invention and its use.

II. Treating Means

The treating means of the present invention comprises a chamber containing a biospecific polymer which may or may not be bound to a support member.

Figure 1:
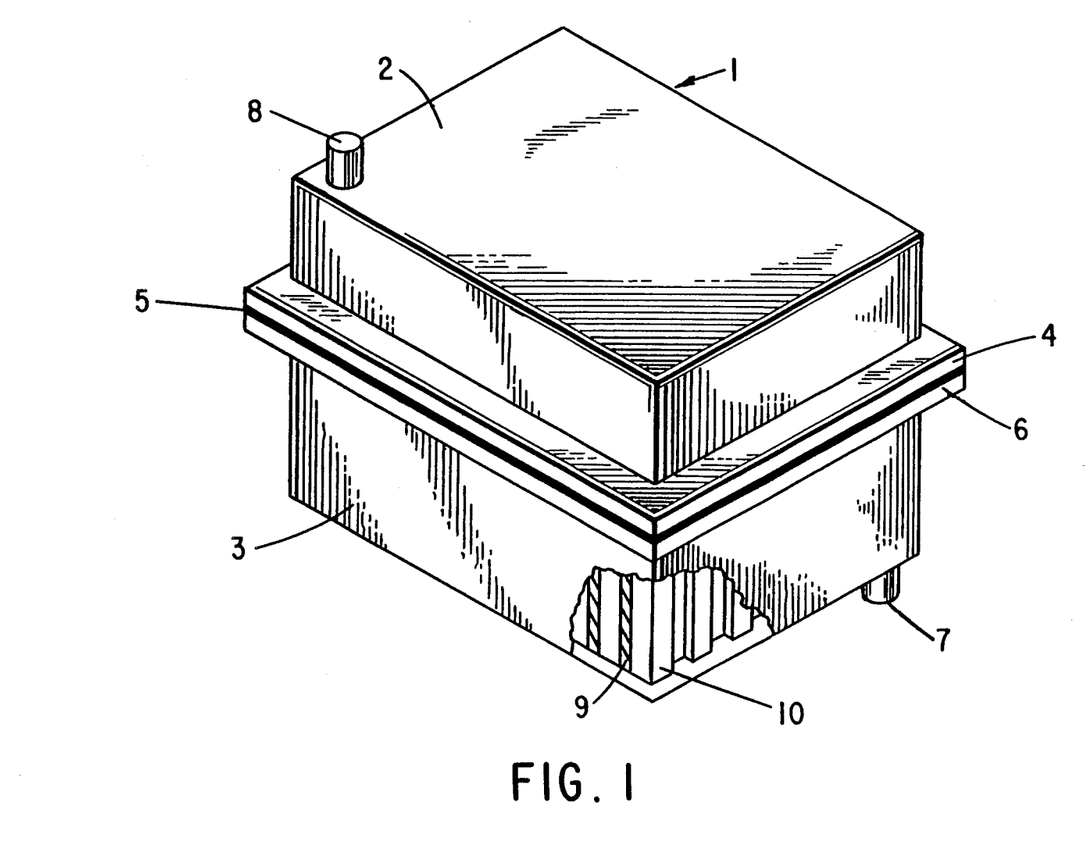
FIG. 1 is a perspective view in partial cut away of a box-like embodiment of a therapeutic device incorporating a biospecific polymer.
Figure 2:
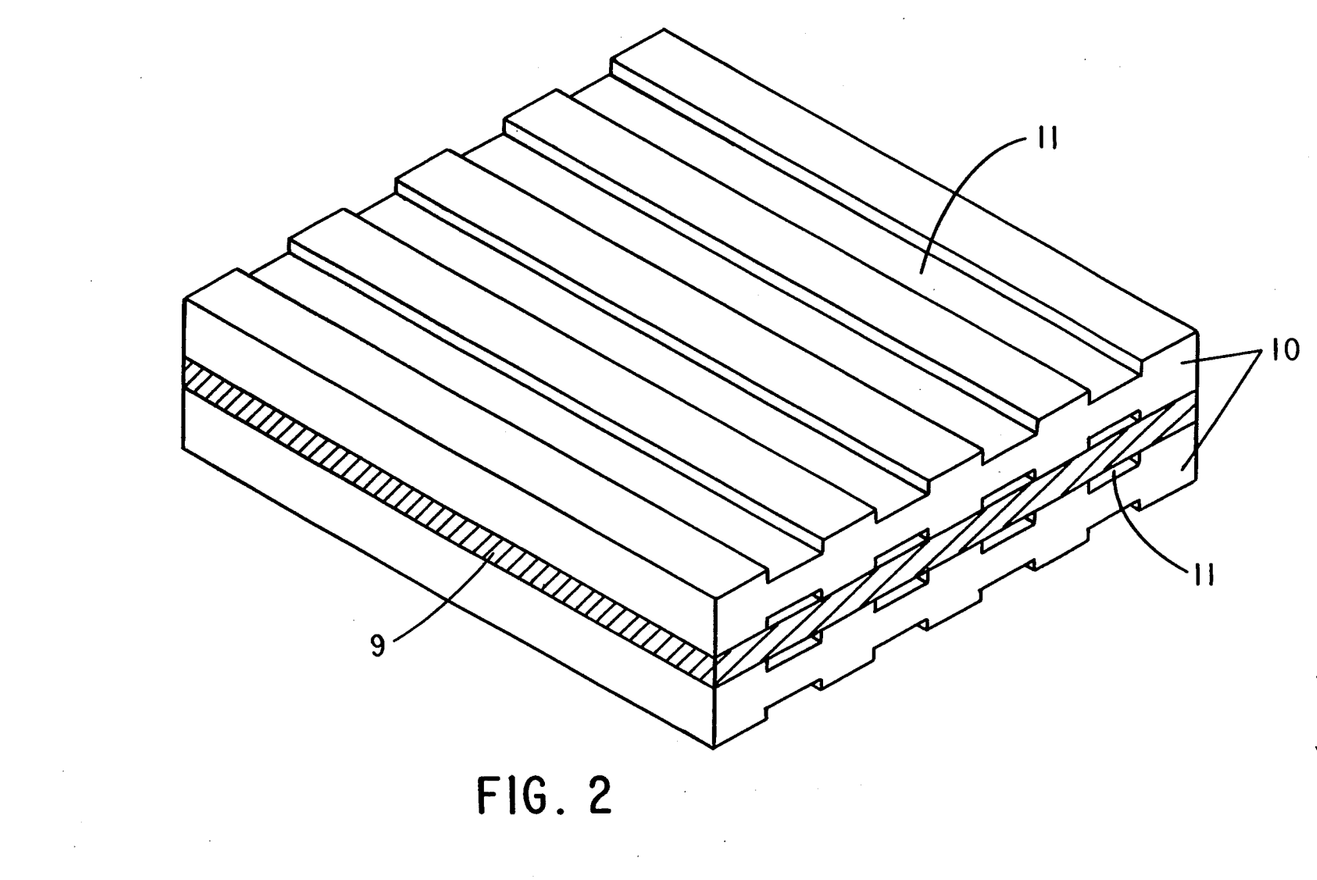
FIG. 2 is a perspective view of a biospecific polymer in a flat sheet configuration with inert separator plates.

Chambers suitable for use in the practice of the instant invention may take many forms. Referring to FIG. 1, a chamber 1 is of a box-like configuration consisting of top shell 2 and bottom shell 3 having upper and lower sealing flanges 4, 6 with sealing means 5 therebetween. Any means for sealing may be employed, i.e., gasket, TEFLON seal, heat sealing, etc., with the caveat that no leakage occurs. A pipe-like or nipple-like fluid inlet 7 and fluid outlet 8 ports protrude from the top and bottom shells of the chamber 1. Within the box-like chamber 1 are a plurality of alternating layers of biospecific polymer sheets 9 and inert separator plates 10. Referring to the biospecific polymer sheets and inert separator plates in greater detail, FIG. 2 illustrates the inert separator plates 10 with fluid flow channels 11 through which the body fluid may flow. The biospecific polymer sheet 9 is held therebetween whereby the fluid flow channels 11 perform to channel body fluid between the biospecific polymer sheet and inert separator plates. It should be apparent that a plurality of inert separator plates and biospecific polymer sheets could be stacked horizontally or placed side-by-side within a chamber. Depending on the amount of biospecific polymer surface area needed for treatment of the body fluid, the number of biospecific polymer sheets and inert separator plates employed may be reduced or increased.

Referring back to FIG. 1, the body fluid to be treated enters the chamber 1 through fluid inlet port 7 and passes into a head space (not shown). From the head space, the body fluid passes in contact with biospecific polymer 9 by way of fluid flow channels 11. The body fluid then passes into a second head space (not shown) and finally exists the chamber through fluid outlet port 8. The head spaces function as a resevoir for the body fluid entering and exiting the chamber.

The inert separator plates should be mechanically stable and sterilizable as well as compatible for use in a system which is in continual contact with body fluids. Examples of materials which are suitable for the practice of the present invention as inert separator plates are, for example, polypropylene, polyethylene, polyurethane, polycarbonate, ABS (acrylonitrile-butadiene-styrene), polysiloxane, and polystyrene. The configuration of the inert separator plates with fluid flow channels is not critical, with the caveat that a sufficient fluid flow configuration is provided eliminating shear forces on the body fluid while maintaining a fluid flow pathway allowing the pathological effectors carried within the body fluid to efficiently diffuse throughout, therefore, eliminating potential damages to the cellular components of the body fluid and maximizing the contact frequency between the pathological effectors and biospecific polymer.

Figure 3A:
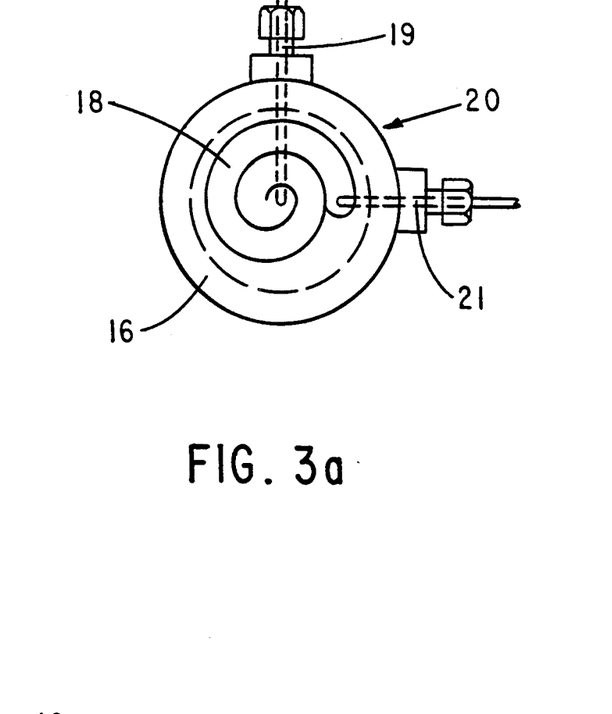
FIG. 3(a) is a top elevational view and FIG. 3(b) is a side elevational view of a spiral flow therapeutic device incorporating a biospecific polymer.
Figure 3B:
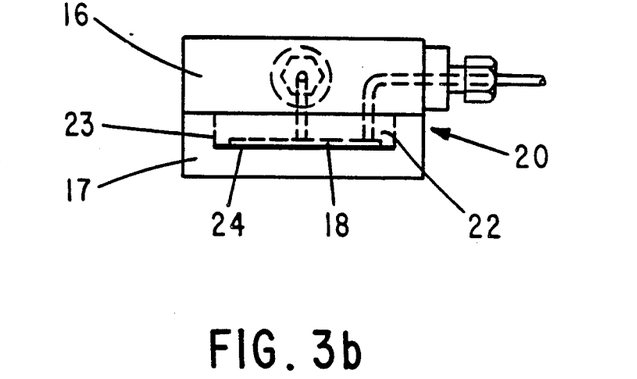

An equally preferred chamber configuration suitable for the practice of the present invention is illustrated in FIG. 3. FIG. 3a illustrates the top part 16 of a chamber 20 with an integral spiral fluid flow channel 18 having fluid inlet port 19 and fluid outlet port 21. FIG. 3b illustrates the chamber 20 with top part 16 and a bottom part 17. The top part 16 has a protruding portion 22 which includes the integral spiral fluid flow channel 18. The bottom part 17 includes a recess 23 having a biospecific polymer sheet 24 received therein. The recess 23 and protrusion 22 are physically configured wherein the protrusion is closely received in the recess. The spiral fluid flow channel 18 performs to channel fluid between the biospecific polymer sheet and protrusion 22.

Figure 4:
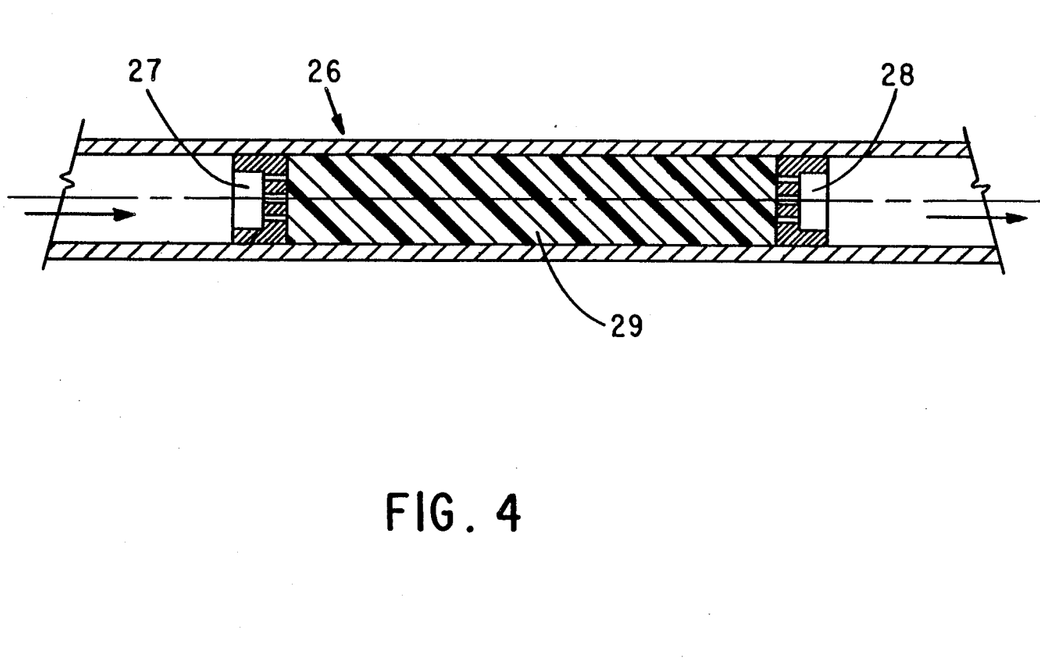
FIG. 4 is a side elevational view in cross section of a cylindrical therapeutic device incorporating a reticulate foam coated with a biospecific polymer.

Another chamber configuration useful in the practice of the present invention is illustrated in FIG. 4. A cylindrical chamber 26 with fluid inlet port 27 and fluid outlet port 28 is shown. The cylindrical chamber 26 contains therein a porous reticulated foam 29 with biospecific polymer (not shown) coated thereon. The porous reticulated foam may be described for the purpose of the present invention as a polymer matrix of contiguous open cells forming fluid flow channels throughout said polymer matrix. The walls of the fluid flow channels are coated with a biospecific polymer whereby the body fluid flowing through such channels is in contact with the biospecific polymer.

The reticulated foam may be any suitable polymeric foam which is curable to a porous, mechanically stable, and sterilizable polymer matrix. Such foams must also be biocompatible.

Figure 5A:
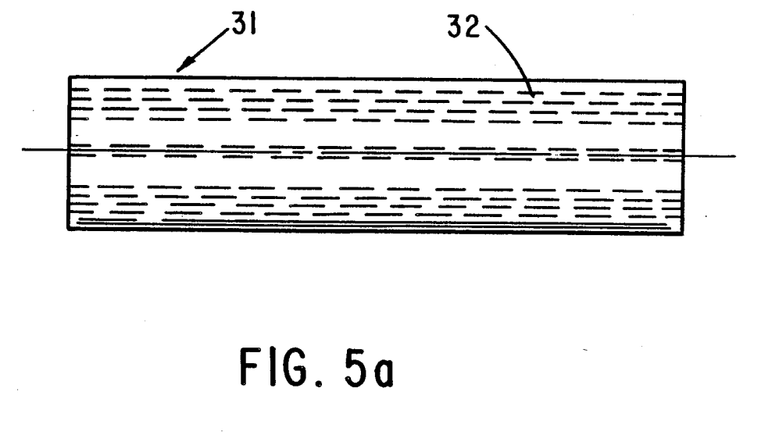
FIG. 5(a) is a side and FIG. 5(b) is an end elevational view of a cylindrical configuration of a biospecific polymer.
Figure 5B:
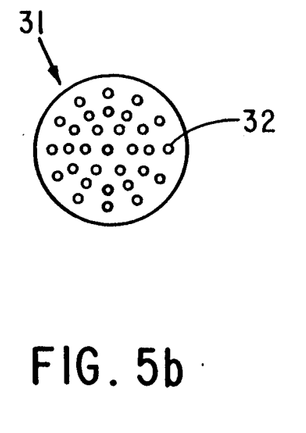
Figure 6:
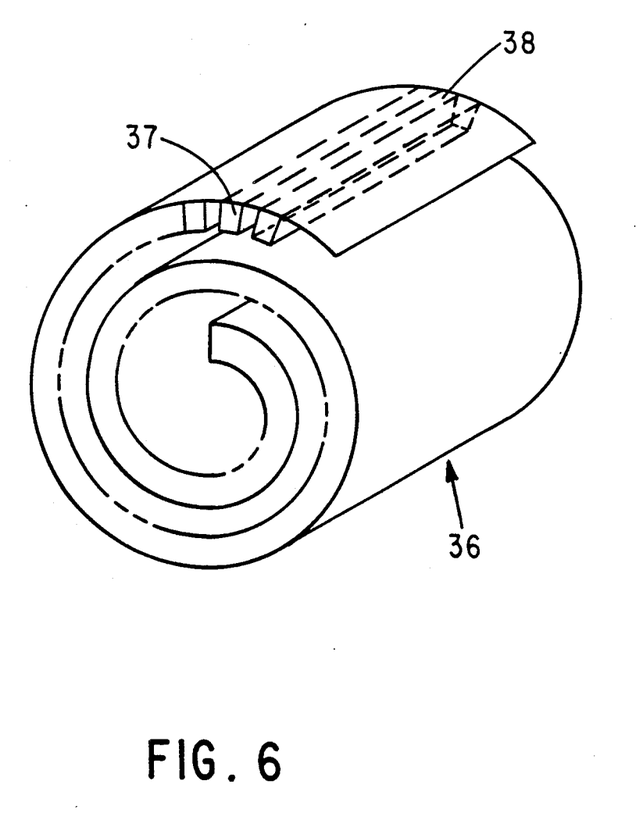
FIG. 6 is a perspective view of a cylindrical spiral configuration of a biospecific polymer.

It is to be appreciated that the configuration of the chamber used in the practice of the present invention does not limit the configuration of the biospecific polymer contained therein. Thus, for example, a box-like chamber may contain a biospecific polymer in a channeled cylindrical configuration or a channeled spiral cylinder configuration respectively illustrated in FIGS. 5 and 6. FIG. 5 illustrates a cylindrical biospecific polymer matrix 31 containing fluid flow channels 32 therethrough. FIG. 6 illustrates a spirally configured biospecific polymer cylinder 36 with integrally formed ribs 37 forming fluid flow channels 38. The ribs 37 may or may not be the same polymer composition as 36.

In still another configuration, the biospecific polymer may be formed into a plurality of spherical beads that are situated within a chamber. As the body fluid passes into the chamber and up through these beads, the beads become fluidized, i.e., they separate from each other in the body fluid—maximizing channeling and effecting more efficient contact between the biospecific polymer and the body fluid. This configuration is known as a fluidized bed.

The fluid flow channels through any of the foregoing embodiments of the biospecific polymer may be of any configuration, again with the caveat that a sufficient fluid flow configuration is provided eliminating shear forces on the body fluid while maintaining a fluid flow pathway allowing the pathological effectors carried within the body fluid to efficiently diffuse throughout, therefore, eliminating the damages to the cellular components of the body fluid and maximizing the contact frequency between the pathological effectors and biospecific polymer.

III. Mechanical Support

Figure 7:
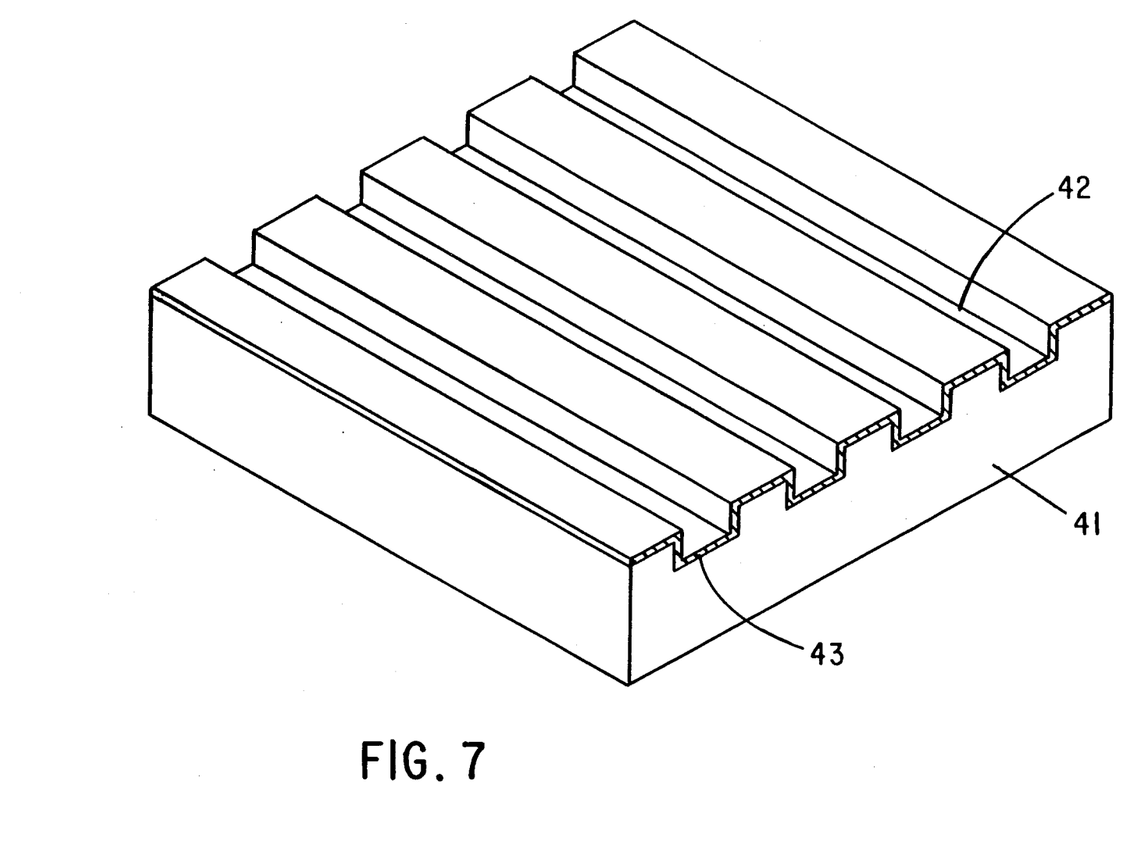
FIG. 7 is a perspective view of a mechanical supporting element having an applied coating of a biospecific polymer.

Most of the biocompatible polymer supports have very low mechanical stability. Most of these materials are, in fact, gels or gel-like as opposed to materials which have high mechanical stability, such as, for example, sheets of polypropylene. Thus, in most embodiments utilizing the present invention, a support member which is mechanically stable is necessary. This support member allows large surface areas to be utilized to insure rapid and medically, as well as commercially, acceptable levels of immune disease-associated component removal. The support member, besides being mechanically stable, should also be inexpensive and must be sterilizable so as to be made compatible for use in a system wherein the blood of a diseased patient is to be treated by the present invention. Examples of materials which are suitable for the present invention as support members include, for example, filter paper, cotton cloth, polyester fiber, reticulated polymeric foams, microporous polypropylene and other polymers including polycarbonate, polystyrene, ABS (acrylonitrile-butadiene-styrene), NORYL, a polyphenylene oxide polymer manufactured by the General Electric Company, and polysiloxanes. FIG. 7 illustrates a mechanical supporting element (41) with fluid flow channels (42) and biospecific polymer (43) fixed thereon by any of the methods discussed hereinbelow. It should be evident that a plurality of mechanical supporting elements with biospecific polymer coatings could be horizontally stacked or placed side-by-side within the chamber providing an increased surface area contacting the body fluid. It should also be evident that the inert separator plates, discussed hereinabove, with the biospecific polymer clamped therebetween would also provide mechanical support for the flat sheet embodiments of the biospecific polymer.

Many methods of fixing the biospecific polymer onto the mechanical support may be utilized. Thus, for example, methods such as spin coating-casting, horizontal casting, vacuum impregnating, dip coating, dip coating with later cross-linking, spray coating, and solution copolymerization may be used.

IV. Biocompatible Polymer Support

The biocompatible polymer supports useful in the present invention are materials which tend not to cause adverse effects when in contact with body fluids, while at the same time maintaining a reactive but immobilized biological oriented such that the biological is extending out from the surface of said polymer support. The materials which are suitable are those which may be cast into films and other physical forms, while at the same time being susceptible to having said biologicals covalently bound to them without damaging either themselves or the biologicals bound thereto. The types of materials generally contemplated to be suitable are those known in the art as hydrogels and may be either copolymers or homopolymers.

Modified cellulose and cellulosic derivatives, particularly cellulose acetate, have also found utility as biocompatible supports useful in the present invention. By modified cellulosic derivatives what is meant is that the cellulosic polymer is surface modified by covalently linking pendant biocompatible surface groups to the cellulosic substrate polymer rendering it more biocompatible. Such surface groups are well known and need not be described here, however, for purposes of the present invention, albumin has shown particular utility as a modifying group. Methods of attaching such groups are described hereinbelow.

Referring to the hydrogels, suitable polymers may either be regular homopolymers containing substantially no other material in their matrices, or they may be copolymers which contain monomers such as styrene and vinyl acetate, for example. In certain instances, this type of tailoring of the copolymers with various monomers may enhance the desirable properties of the biocompatible polymer support material. Examples of suitable monomers which may be copolymerized include, for example, N-vinyl pyrrolidone and glycidyl methacrylate.

Homopolymers may also be used as suitable biocompatible polymer supports in the present invention. It is to be understood, however, that when homopolymers are discussed, they include materials which can also be identified as "slightly cross-linked homopolymers." That is, they contain a minor amount of a second component either intrinsic in the production of the monomer or added purposely to insure enough cross-linking so as to protect the homopolymer from slowly dissolving away in an aqueous media, such as blood. An example of this type of homopolymer which is often slightly cross-linked is hydroxyethyl methacrylate (HEMA).

Also useful are terpolymers which are a subclass of copolymers containing three monomers which are polymerized. An example of a suitable terpolymer is glycidyl methacrylate/N-vinyl pyrrolidone/hydroxyethyl methacrylate (GMA/NVP/HEMA).

In addition to the specific copolymers and homopolymers listed above, copolymers and homopolymers suitable in the present invention may be polymerized from the following monomers: hydroxyalkyl acrylates and hydroxyalkyl methacrylates, for example, hydroxyethyl acrylate, hydroxypropyl acrylate, and hydroxybutyl methacrylate; epoxy acrylates and epoxy methacrylates, such as, for example, glycidyl methacrylate; amino alkyl acrylates and amino alkyl methacrylates; N-vinyl compounds, such as, for example, N-vinyl pyrrolidone, N-vinyl carbazole, N-vinyl acetamide, and N-vinyl succinimide; amino styrenes; polyvinyl alcohols and polyvinyl amines, which must be made from suitable polymeric precursors; polyacrylamide and various substituted polyacrylamides; vinyl pyridine; vinyl sulfonate and polyvinyl sulfate; vinylene carbonate; vinyl acetic acid, and vinyl crotonic acid; allyl amine and allyl alcohol; vinyl glycidyl ethers and allyl glycidyl ethers. Processes and procedures for creating copolymers and/or homopolymers from the above monomers are well-known and understood in that particular art. These parameters are not critical to the instant invention with the caveat that the final copolymer and/or homopolymer is nontoxic for animal, including human, use.

The biocompatible polymers utilized in this invention are to be distinguished from those produced by radiation grafting techniques. The latter, which are generally synthesized using high energy radiation (gamma radiation, x-rays, electron beams and the like), are completely different in structure from those disclosed in out invention, particularly when more than one monomer is involved. Due to the nature of high energy radiation, radiation grafting and polymerization in general occur in an uncontrolled and indiscriminate fashion. Thus, when a polymeric substrate such as our mechanical support is bombarded with gamma radiation in the presence of one or more monomers, a multiplicity of structures is produced with very complex topography. This complexity is, of course, greatly enhanced when two or more monomers are available for reaction, and depending on such diverse factors as monomer relative reactivities and sensitivity of the various monomeric and polymeric species to radiation, the functional groups needed for bioactivation may not be available consistently in pracitcal concentration at the polymer surface. This imposes a considerable limitation on the choice of mechanical supports. It is also well known that may polymers are degraded under radiation grafting conditions and can, under certain conditions, evolve toxic moieties. Finally, it should be realized that radiation grafting creates an entirely new composition which is similar to a composite or an alloy, especially at the critical graft/substrate interface. A successful radiation graft copolymerization requires substantial penetration of the grafted polymer into the substrate with random covalent bonding among all available components. The resulting structure is chemically and physically different than any of the starting materials. For these reasons, application of radiation induced graft copolymerization to the manufacture of the biocompatible polymers of the present invention wound be commercially impracticable.

In contrast, the biospecific polymers utilized in this invention are made by techniques which employ mild and controlled conditions. The synthesis of the biocompatible polymer support is not restricted to polymerization in the presence of the mechanical support, but may also be carried out as an entirely separate operation so that grafting is clearly unnecessary. The only major physical requirement is that the biocompatible polymer be in a state such that it can form a continuous and reasonably adherent coating on the mechanical support. As a result of these factors, the supporting polymeric structures perform only the separate functions implied by their names and, under suitable conditions, can even be stripped away from each other for analysis and physical studies if desired. Thus, the biocompatible polymeric system of the invention is well adapted to the tailoring demanded by the specificity of the ultimately attached biologicals. In addition, no problems are posed in device construction on any scale, since as has already been suggested, a variety of well known methods may be used to coat the mechanical support with the biocompatible support.

V. Biologicals

In the context of the present invention, biological and/or biologicals may be defined as a chemical compound which possesses an ability to covalently bond to the biocompatible polymer support or spacer (defined hereinbelow), while at the same time retaining an activity to bind a desired pathological-causing constituent. It is to be understood that, in addition, the biological or biologicals employed must be of such size that they covalently bond to the surface of the polymer support and are not small enough to penetrate the porous matrix of the polymer support and be chemically bonded therefore inside or in the interior of the support material. In this light, a spacer may be employed to insure that the reactive site of the biological, which remains and is susceptible to bonding with the desired pathological constituent, can in fact be presented to this constituent, i.e., that it is held outward away from the support so as to come into contact with the body fluid flowing over the support. It is obvious from the above that, of course, the reactivity for binding the desired pathological constituent is, in fact, retained after immobilization of the biological or biologicals onto the biocompatible polymer support. Examples of materials which may be used as biologicals include, for example: acetylcholine receptor proteins, histocompatibility antigens, ribonucleic acids, basement membrane proteins, immunoglobulin classes and subclasses, myeloma protein receptors, complement components, myelin proteins, and various hormones, vitamins and their receptor components. Particular examples are, for example, attaching insulin to a biocompatible polymer support to remove anti-insulin antibody which is associated with the autoimmune disease insulin resistance; attaching anti-Clq and/or Clq to a biocompatible polymer support to remove immune complexes which are associated with connective tissue and proliferative diseases such as, for example, rheumatoid arthritis and carcinomina.

Any generally known method of chemical attachment will suffice for attaching the biologicals to the biocompatible polymer support, with the caveat that the biological still has at least one active site for the particular autoimmune disease-associated component. Generally, the methods of chemical attachment used fall into three classes or routes of attachment. These three routes are, (1) spontaneous attachment, (2) chemical activation of terminal functional groups, and (3) coupling reagent attachment. Spontaneous covalent attachment of biologicals to polymer support surface proceeds via chemically reactive groups extending from the polymer support. Thus, for example, reactive groups such as aldehyde and epoxy extending from the polymer support readily couple biologicals containing available hydroxyl, amino or thiol groups. Also, for example, free aldehyde groups on the polymer support couple via acetal linkages with hydroxyl-containing biologicals and via imide linkages with amino-containing molecules. Additionally, for example, free oxime groups couple via alkylamine, ether and thioether linkages with biologicals containing amine, hydroxyl and thio groups respectively. For purposes of convenience all said attachments and couplings are defined herein as immobilizations. More extensive discussions of these reactions may be found, for example, in "Chemical Procedures for Enzyme Immobilization of Porous Cellulose Beads," Chen, L. F. et al, Biotechnology and Bioengineering, Vol. XIX , pp. 1463–1473 (1977) and "Epoxy Activated Sepharose," 6B, Parmacia Fine Chemicals, Affinity Chromatography, pp. 27–32 (1979).

Chemical activation of terminal functional groups may be accomplished by activating polymer surface functional groups by chemical modification of their terminal components. This method can be exemplified by the oxidation of terminal epoxy functions with periodic acid to form active aldehyde groups. This method is further exemplified, for example, in "Immobilization of Amyloglucosidose on Poly [(Glycidyl Methacrylate) Co (Ethylene Dimethacrylate)] Carrier and Its Derivatives," Svec, F. et al, Biotechnology and Bioengineering, Vol. XX, pp. 1319–1328 (1978). The immobilization of the biologicals proceeds as described hereinabove. Condensation reactions may be accomplished between free carboxyl and amine groups via carbodiimide activation of the carboxy groups as is described, for example, in "New Approaches to Non-Thrombogenic Materials," Hoffman et al, *Coagulation—Current Research and Clinical Applications,* Academic Press, N.Y. (1973). Briefly the immobilization of the biologicals is effected by carbodiimide activation by either the polymer or biological carboxyl groups and condensation with a free amine to form a stable peptide bond. The final orientation of the biological is generally a factor as to whether an amine or a carboxyl containing polymer be utilized.

Coupling reagent attachment can be accomplished using a variety of coupling agents to form covalent bridges between polymers and biologicals. Here free hydroxyl and/or amine containing polymers and biologicals are covalently coupled by reagents such as, for example, cyanogen bromide, diisocyanates, dialdehydes and trichloro -s-triazine. More exhaustive discussion of this technique may be found for example, in the Chen et al article cited hereinabove.

The preferred method of immobilizing a reactive biological onto a biocompatible polymer substrate in a given case generally is dictated by the molecular locations of the reactive binding moiety of the biological and the functional groups on the biological and polymer substrate which can be covalently combined. For example, it is presently preferred in the case of polymer substrates containing terminal hydroxy functions to activate by treatment with an alkaline solution of cyanogen bromide (10 to 20% w/v). Typically the reaction mixture is maintained at room temperature (20° to 25° C.) for about 30 minutes. The pH of the solution is maintained in a range of about 10 to 12, by the addition of alkaline material, e.g., KOH or NaOH. The polymer is extensively washed with physiological saline (0.9 gm%) and incubated with solutions of a purified biological dissolved in a slightly alkaline buffer solution for 12 to 16 hours at 2° to 8° C. The polymer is extensively rinsed with physiological saline to remove unbound or nonspecifically bound biological components.

Biologicals are immobilized on glycidyl containing polymers via ether, thioether or alkylamine bonds. Epoxy-activated polymer substrates are rinsed and swollen with aqueous neutral buffer solutions at room temperature. Purified biologicals, dissolved borate, carbonate or phosphate buffer solutions are incubated with the glycidyl polymer substrate for 12 to 20 hours at 4° to 30° C. Excess and nonspecifically bound biologicals are removed by rinsing the polymer with saline, acetic acid (0.2 to 1.0M) and phosphate-buffered (pH=7.2±0.2) saline solutions. Activation of amine and carboxyl containing polymer matrices is effected by treatment with purified biologicals dissolved in slightly acidic (pH 4.5 to 6.5) buffer solutions of a water soluble carbodiimide. Biologicals are covalently coupled to polymer support substrates by incubation of polymer support, biological and carbodiimide reactants for 12 to 16 hours at 2° to 8° C. The polymer-biological conjugates are washed alternately in acid then alkaline rinses until the rinse solutions are clear of biological and carbodiimide reactants.

In order to determine the specific binding characteristics of the polymer immobilized biologicals, physiological serum solutions of complementary biomolecules were treated with activated membranes. The amounts of biomolecule were measured spectrophotometrically and radiochemically. Significant reduction of specific biomolecules resulted following brief exposures to the biologically modified polymer substrates.

VI. Spacers

In the present invention, a spacer may be defined as a molecule or compound which is capable of attachment to the surface of a biospecific polymer support, is large enough to extend from the surface of said support and is capable of immobilizing a biological and/or biologicals. The spacer insures that the active site of the biological is held outward away from the support so as to contact the body fluid more efficiently. It is obvious from the above that, of course, the reactivity for binding with the desired disease complex is, in fact, retained after immobilization of the biological or biologicals onto the spacer and therefore onto the biocompatible polymer support.

The spacers are derived from organic molecules having at least two reactive functional groups generally situated at opposing ends of the molecule. Such groups serve as attachment vehicles capable of coupling the spacer to the polymer support and to the biological. The reactive functional groups on the spacer may be the same or different with the caveat that they react with functional groups along the surface of the polymer support and functional groups extending from the biological forming covalent bonds. Any known method for carrying out such coupling reactions will suffice. For example, the methods described hereinabove outlining coupling routes for attaching a biological directly onto a polymer support may be used.

Suitable examples of spacers which may be used in the present invention, where the reactive functional groups are the same, include, for example, 1,6-diaminohexane, divinyl sulfone, glutaraldehyde, 1,4-cyclohexanedicarboxylic acid, ethylenediamine tetraacetic acid, triethylene glycol, 1,4-butanediol diglycidyl ether, methylene-p-phenyl diisocyanate and succinic anhydride. Examples of spacers in which the reactive functional groups are not the same include, for example, 6-aminocaproic acid, p-nitrobenzoyl chloride, 1,2-epoxy-3-(p-nitrophenoxy) propane, aminopropyltriethoxy-silane and homocysteine thiolactone.

Polypeptides and more specifically proteins may also be used as spacers in the present invention. Albumin, a low affinity protein, for example, has been successfully employed as a spacer. In addition, albumin and other natural proteins serve to render the polymer support more biocompatible.

Finally, it is understood that certain materials may act simultaneously as a spacer and as the activator in the reaction used to combine the spacer and the biocompatible support. Examples of these kinds of compounds, include, for example, gluteraldehyde and 1,4-butanediol diglycidyl ether.

VII. Therapeutic Regimen

Broadly stated, the contemplated therapeutic regimen of the present invention is for the treatment of (autoimmune and other) diseases by exposing a diseased patient's blood to a biospecific polymer having immobilized reactive biologicals, thereby removing the specific pathological effectors from said patient's blood and then returning said blood to said patient; characterized in that said biospecific polymer comprises: (a) a biocompatible polymer support, (b) a biological or biologicals immobilized on said biocompatible polymer support, via chemical bonding, characterized in that the biological or biologicals retain their reactivity for binding the specific pathological effectors or specific group of pathological effectors associated with said patient's particular disease or diseases. This therapeutic treatment may or may not necessitate the use of blood separation techniques. Thus the treatment is contemplated to be carried out in a manner similar to a dialysis treatment with the advantage that total blood separation may not be needed and that there is very little if any physical damaging of normal blood components.

It is also possible, of course, to utilize the present invention and the process of the present invention in the treatment of plasma. The plasma may be obtained from whole blood by any of the currently known and practiced methods. Thus, for example plasma may be separated from a patient's blood by known methods, then treated by the present invention and then recombined with the other blood components and returned to the patient using currently known procedures. In addition plasma which is being used in known medical treatments may utilize the present invention to treat said plasma before being administered to a patient requiring plasma from a blood bank, for example. Obviously whole blood from a blood bank may also be treated by and benefit from the present invention.

Because of the advantages of the present invention mentioned above as well as others which will be clear to a person skilled in this art many types of disease states are contemplated to respond to the present invention used in a therapeutic regimen. Broadly stated six groups of disease states could be advantageously treated. These six disease categories are disorders of immune components, drug excesses, toxin exposure, imbalances of body substances, infections, and neoplastic states. Many diseases are currently treated using plasmapheresis and cytopheresis where the desired result is removal of a specific substance. The present invention and the process of the invention would apply to these diseases currently treated by plasmapheresis and cytopheresis.

Examples of immune complex diseases which can be treated are, for example, any disease states involving antibody, antigen, antibody-antigen, antigen-antigen and antibody-antibody interactions, cell surface complexes, cytoplasmic complexes, etc.

Examples of drug overdoses which can be treated are, for example, overdoses of iron, dioxin, aspirin, TYLENOL ®, methotrexate and other tricyclics.

Examples of toxins for which the present invention is suitable are, for example, lead, aluminum, mushrooms (Anatoxin) and organic phosphates.

Body substances when present in excess can lead to disease. Examples of these which can be eliminated using the present invention include, for example, cholesterol, uric acid, immunoglobulins, sickle cells, uremic toxins, bilirubin, porphyrin, cortisol and prostaglandins.

Some examples of infectious agents which may be treated are, for example, viral disorders such as cytomegalovirus; protozoan disorders such as malaria, trypanosomes and leishmanias; bacterial infections such as strepotococci; fungus infections such as tinea versicolor; mycoplasma such as pleuro-pneumonia-like organisms; rickettsia diseases such as typhus and spotted fevers; spirochetes such as syphilis and chlamydia-agents in the psittacosis lympho-granuloma-trachoma disease group.

Neoplasms which are treatable using the present invention include, for example, the lymphomas, sarcomas, carcinomas and leukemias. These may be removed by specific removal of a cell line, inhibitors, initiators of the disease and combinations thereof.

Further examples of disease states which may be treated using the present invention include, for example, the following:

Infections such as; Post streptococcal glomerulonephritis, Subacute bacterial endocarditis, Secondary syphilis, Pneumococcal sepsis, Lepromatous leprosy, Ventricular shunt infection, Infectious mononucleosis, Typhoid fever, Subacute sclerosing encephalitis, Landry-Guillain-Barre syndrome, Hepatitis B infection, Quartan malaria, Schistosomiasis, and Trypanosomiasis.

Neoplasmas such as; Hepatoma, Lymphoma and Hodgkins disease, Acute leukemia, Hypernephroma, Carcinoma of the colon, Bronchogenic carcinoma, and Burkitts lymphoma.

Connective Tissue Disorders such as; Periarteritis nodosa, Chronic glomerulonephritis, Acute or subacute thyroiditis, Vinyl chloride poisoning, Chronic liver disease, Mixed cryoglobulinemias, Berger's disease or IgA nephropathy, Rapidly progressive glomerulonephritis, and Sickle cell anemia.

Hematologic Diseases such as; Thrombic thrombocyto-penic purpura, Autoimmune hemolytic anemia, Idiopathic thrombocytopenic purpura, Idiopathic neutropenia, Cold hemagglutinin disease, Paroxysmal cold hemoglobinuria, Circulating anticoagulants, Acquired hemophilia, the leukemias, the lymphomas, Erythro-blastosis fetalis, Pernicious anemia, and Rh diseases.

Neurologic Diseases such as; Acute demyelinating encephalitis, Multiple Sclerosis, Landry's paralysis, Guillain-Barre syndrome, Peripheral neuritis, and Myasthenia gravis.

Collagen Diseases such as; Raynaud's, Lupus Erythematosus, Polyarteritis nodosa, Scleroderma, Dermatomyositis, Sjogren's syndrome, Rheumatoid arthritis, Rheumatic fever, and Erythema nodosa.

Endocrine Diseases such as, for example; Cushing's syndrome & disease, Thyroiditis, Thyrotoxicosis, Addison's disease, and Aspermatogenesis.

Gastrointestinal Diseases such as; Portal cirrhosis, Acute hepatitis, Chronic active hepatitis, Lupoid hepatitis, Biliary cirrhosis, Ulcerative colitis, Regional enteritis, and Pancreatitis.

Miscellaneous Diseases such as, for example; Hypercholesterolemia, Glomerulonephritis, Basement membrane disease, Psychogenic states—drugs, Postaortic valve prosthesis—hemolytic anemia, Exfoliative dermatitis, Id reaction, Psoriasis, Behcet's syndrome, Thrombotic thrombocytopenic purpura, Carcinoma, Subacute bacterial endocarditis, Hypertension, Asthma, Hereditary angioneurotic edema, Meningococcemia, Crohn disease, Hepatic encephalopathy and Raynaud disease.

Further, Diseases characterized by Antibodies to Nuclear Antigens, Cytoplasmic Antigens, Cell Surface Antigens, and Subclasses may be treated by the present invention. Suitable examples include, for example; Antibodies to Native-DNA (double stranded) or single and double, stranded Antibodies to SS DNA, Antibodies to Deoxyribonucleoprotein, Antibodies to Histone, Antibodies to Sm, Antibodies to RNP, Antibodies to Sc 1—1 -Scleroderma, Antibodies to SS-A Sjogren syndrome, Sicca complex, Antibodies to RAP - Rheumatoid Arthritis, Sjogren syndrome, Antibodies to PM-1 -Polymyositis-dermatomyositis, and Antibodies to nucleolarSystemic sclerosis, Sjogren syndrome.

Also, Antibodies Associated With Specific Autoimmune Disorders such as; Antibodies to smooth muscle - Chronic Hepatitis, Antibodies to acetylcholine receptors Myasthenia gravis, Antibodies to basement membrane at the dermal-epidermal junction - Bullous pemphigoid, Antibodies to the mucopolysaccharide protein complex or intracellular cement substance Pemphigus, Antibodies to immunoglobulins - Rheumatoid arthritis, Antibodies to glomerular basement membrane Glomerulonephritis, Goodpasture's syndrome, Idiopathic primary hemasiderosis, Antibodies to erythrocytes - Autoimmune hemolytic anemia, Antibodies to the thyroid - Hashimoto's, Antibodies to intrinsic factor - Pernicious anemia, Antibodies to platelets - Idiopathic thrombocytopenic purpura, Alloimmunization, Antibodies to mitochondria - Primary biliary cirrhosis, Antibodies to salivary duct cells - Sjogren's syndrome, Antibodies to the adrenal - Idiopathic adrenal atropathy, Antibodies to thyroid microsomal Grave's Disease, Antibodies to thyroglobulin - Addison's Disease, and Antibodies to islet cells - Diabetes Mellitus.

Paraproteinemias such as, for example, Multiple myeloma, Macroglobulinemia, Cryoglobulinemia, and Light chain disease;

Hyperlipidemia such as, Primary biliary cirrhosis and Familial Hypercholesterolemia;

Endocrinopathies such as, Grave disease and Diabetes mellitus;

Alloimmunization such as, Hemolytic disease of the newborn and Renal homograft rejection.

Also, suitable for treatment using the present invention include, for example, Post Transfusion Purpura and Autoantibody Diseases such as, Goodpasture's syndrome, Myasthenia gravis, Pemphigus vulgaris, Hematological disease, Idiopathic (autoimmune) thrombocytopenic purpura, Autoimmune hemolytic anemia, Inhibitor to factor VIII and Polyradiculopathy/Guillain-Barre Syndrome.

Immune Complex Diseases may also be treated and include, for example; Systemic lupus erythematosus, Polyarteritis nodosa, Cutaneous vasculitis, Rheumatoid arthritis, Glomerulonephritis, and Dermatomyositis.

While not subscribing to any one particular theory over another, a review of the probable progression of autoimmune pathology suggests that the pathological sequence is very likely initiated by a free antigen -challenge, followed by antibody evolution and complexing and finalized by antibody excess and complement fixation of formed complexes. Thus, for proper selection of the biospecific polymer formulation and provision for proper efficacy would require preliminary diagnostic procedures to determine the predominant form of the autoimmune effector. An illustrative example of this is described below for the treatment of rheumatoid disease. Briefly, rheumatoid disease can be characterized as following the progression from (a) free RF antigen (atypical Ig) (rheumatic condition),(b) free RF antibody evolution and RF complexing and finally (c) antibody excess and complement activated RF complex fixation. Thus treatment of rheumatoid disease in its early development could be determined by detection of atypical immunoglobulins by monoclonal rheumatoid factor (m-RF) antibodies. Treatment at this stage would be best effected by m-RF activated biospecific polymers to remove the offending antigen and thus prevent the evolution of endogenous RF (e-RF) antibodies. Diagnostic evidence of e-RF would indicate the utilization of biospecific polymers having both m-RF and aggregated gamma globulin active biologicals (RF antigen). Alternatively, two biospecific polymers in series, each having one type of active biological could be utilized. In either case this combination of m-RF and aggregated gamma globulin would adsorb both the offending antigen and antibody molecules to sequester the disease progression. In the case where significant levels of RF antigen-antibody complex is detected, biospecific polymers containing Clq and/or collagen effector molecules would be indicated. Finally, if the disease process has progressed to the stage of complement fixation of formed immune complexes, an effective biospecific polymer would contain one or more anti-complement antibodies such as, for example, anti-Clq, anti-$C_3$ or anti-$C_4$ Again the biologicals, if more than one is desirable, can be immobilized on a single biocompatible support or each can be on a separate support and connected in series in relation to the blood or plasma flow.

As has been proposed above, effective use of the present invention is realized by thorough definition of the dynamics and stage of the immune response for effective disease management.

Today, plasmapheresis and cytopheresis are the treatments for disease by removal of noxious substances or cells from the blood. It is currently believed that any disease treated by plasmapheresis and/or cytopheresis, where the desired result is the removal of a specific substance, can be advantageously treated with the product and process of the present invention.

More specifically, a presently contemplated therapeutic regimen for whole blood may be illustrated as follows:

(a) a vascular access is provided which will allow for;
(b) a blood flow from about 30 ml/min. to about 200 ml/min.,
(c) an anticoagulant is administered to the blood; and
(d) a pumping means may or may not be provided;
(e) the blood is passed into the chamber device containing therein biospecific polymer membrane(s);
(f) treating the whole blood by passing it in contact with said biospecific membrane;
(g) depending on the anticoagulant used, additional medication may be needed or desired to neutralize the anticoagulatory effect on said treated blood;
(h) the treated blood is returned to the patient.

The time frame presently contemplated for the above regimen is approximately 2 hours to 4 hours. It is realized, of course, that depending on the situation, such a time frame may be either shortened or lengthened.

A presently contemplated therapeutic regimen for plasma may be illustrated as follows:

(a) a vascular access is provided which will allow for;
(b) a blood flow about 30 ml/min. to about 200 ml/min.,
(c) an anticoagulant is administered to the blood; and
(d) a pumping means provided;
(e) a plasma-formed blood component separation means is provided;
(f) the plasma is passed into the chamber device containing therein biospecific polymer membrane(s);
(g) treating the plasma by passing it in contact with said biospecific membrane;
(h) filtration through a 0.2 micron filter to remove any microemboli, bacteria or fungi;
(i) the treated plasma and the formed blood components are recombined;
(j) depending on the anticoagulant used, additional medication may be needed or desired to neutralize the anticoagulating effect on said treated blood;
(k) the treated blood is returned to the patient.

The following example will serve to further illustrate the present invention. This example should not be considered, however, as a limitation upon the scope of the present invention.

EXAMPLE

This example illustrates how a biospecific polymer utilizing a spacer may be produced. It also demonstrates the effectiveness of a therapeutic device embodiment of the present invention for removing rheumatoid factor antibody from test sera.

A. Spacer attachment.

A polymer support consisting of 50 percent glycidyl methacrylate/46 percent n-vinyl pyrrolidone/4 percent hydroxyethyl methacrylate was hydrated by placing the polymer in deionized water for three hours. The hydrated polymer support was then placed in a therapeutic device similar to the device illustrated in FIG. 3. A 10 ml 1.0M ACA solution ph-7.2 was passed through the device contacting said polymer support at a flow rate of 0.33 ml/min. The device was cleared of excess ACA solution and 40 ml of 0.1M (2[N-morpholine]ethanesulfonic acid) (MES) was then passed through the device at a flow rate of 0.33 ml/min allowing the polymer support to equilibrate.

B. Polymer activation/biological immobilization.

The polymer support with pendant ACA spacers contained in the device was treated with 10 ml solution of 1.0M 1-ethyl-3(3-dimethylaminopropyl)carbodiimide (CDI). The CDI was recycled through the device in contact with said polymer support with pendant spacers at a flow rate of 0.5 ml/min. The reaction was allowed to proceed for 30 min. Excess CDI was rinsed from the polymer support by passing a 10 ml solution of 0.2M MES through the device at a flow rate of 2 ml/min.

A 10 ml heat aggregated human gamma globulin (HGG) solution was recycled through the device contacting the activated polymer support at a flow rate of 0.5 ml/min. Said activated polymer support was allowed to react with the aggregated HGG for 72 hours at room temperature giving a biospecific polymer.

C. Evaluation of therapeutic device for removing rheumatoid factor antibody.

Three trials were conducted using three sources of sera positive for rheumatoid factor antibody. For each trial, the device was placed in a fluid flow circuit with a resevoir, pump and in-line valve. The in-line valve was positioned so as to isolate the device from the circuit when engaged. Before each trial the whole circuit was rinsed with 0.05M PBS solution for approximately 24 hours. The device was then isolated from the circuit via the in-line valve. The circuit (excluding the device) was cleared of PBS solution and 6.0 ml of the respective rheumatoid positive control serum was then added to the circuit resevoir and recirculated for approximately 15 min. to prime the circuit. The in-line valve to the device was then disengaged allowing the test serum to recirculate through the full circuit at a flow rate of 0.414 ml/min.[1] At time intervals of 7½, 15, 30, 60 and 120 min., 0.5ml aliquots of test serum was removed from the resevoir to determine rheumatoid factor concentration via nephelometric analysis. The analysis was conducted on a Beckman ICS TM Analyzer II nephelometer. Results are listed in Table I below. After each trial, two separate rinses of 5.0 ml of 1.0M acetic acid was circulated through the device to desorb the bound rheumatoid factor.

[1] The therapeutic device contained 1.5 ml of PBS solution which was allowed to mix with the test sera as the in-line valve was opened.

TABLE I

| | RF POSITIVE CONTROL SERA | | |
|---|---|---|---|
| Time Re Circulated (min.) | LAS-R TM Level I* | Beckman RF Calibrator** Initial Reading (Iu/ml) | Clinical Patient Serum*** |
| | 335 | 400 | 211 |
| 7.5 | 225**** | 163**** | 147**** |
| 15 | 234 | 166 | 154 |
| 30 | 230 | 201 | 154 |
| 60 | 226 | 210 | 155 |
| 120 | 219 | 200 | 156 |

*Product of Hyland Diagnostics
**Product of Smith Kline/Beckman Instruments
***Clinical patient (1185-620) Serum diluted 1:6 with normal human plasma.
****Initial sharp drop due in part to dilution effects.

What is claimed is:

1. A device for the treatment of a body fluid which comprises:
   (a) a means for withdrawing a body fluid from a patient;
   (b) a chamber means for receiving said body fluid having inlet and outlet means;
   (c) positioned within said chamber means a non-radiation grafted biospecific polymer comprising a biocompatible polymer support, a spacer covalently bonded to said biocompatible support, and a biological or biologicals covalently bonded to said spacer such that the biological or biologicals extend away from the surface of said polymer support, which biospecific polymer will chemically bond specific pathological effectors or specific groups of pathological effectors carried by said body fluid to remove said specific effectors therefrom; and
   (d) means for returning said body fluid to said patient.

2. The device as recited in claim 1 wherein the biospecific polymer is of any structural configuration provided that sufficient surface area of the biospecific polymer is exposed to the body fluid to be treated to efficiently remove the desired amount of pathological effector.

3. The device as recited in claim 1 wherein the biocompatible polymer support is a hydrogel.

4. The device as recited in claim 1 wherein the biocompatible polymer support is selected from the group consisting of polymerized glycidyl acrylate, polymerized glycidyl methacrylate and mixtures thereof.

5. The device as recited in claim 1 wherein the biocompatible polymer support is the slightly crosslinked homopolymer hydroxyethyl methacrylate.

6. The device as recited in claim 1 wherein the biocompatible polymer support is selected from the group consisting of copolymerized N-vinyl pyrrolidone and glycidyl methacrylate said copolymer further containing a monomer selected from the group consisting of hydroxyalkylacrylates, hydroxyalkylmethacrylates, acrylamides, substituted acrylamides, vinyl glycidyl ethers, alkylglycidyl ethers, N-vinyl amides, vinyl acetate and mixtures thereof.

7. The device as recited in claim 1 wherein the biologicals are selected from the group consisting of acetylcholine receptor proteins, histocompatibility antigens, ribonucleic acids, basement membrane proteins, immunoglobulin classes and subclasses, myeloma protein receptors, complement components, myelin proteins, hormones and their receptor components and vitamins and their receptor components.

8. The device as recited in claim 1 wherein the biological is insulin used to remove anti-insulin antibody which is associated with the autoimmune disease insulin resistance.

9. The device as recited in claim 1 wherein the biological is purified gamma globulin to remove immune componnets which are associated with connective tissue and proliferative diseases.

10. The device as recited in claim 1 wherein the biocompatible polymer support is modified cellulose acetate.

11. The device as recited in claim 1 further characterized in that said biocompatible polymer support is fixed to a mechanically stable support member.

12. The device as recited in claim 11 wherein the mechanically stable support member is selected from the group consisting of polyester fiber, reticulated polymeric foams, microporous polypropylene, cottom cloth, polystyrene; polycarbonate, polyphenylene oxide, and polysiloxane.

13. A device for the treatment of a body fluid which comprises:
   (a) means for withdrawing a body fluid from a patient; a patient;
   (b) a chamber means for receiving said body fluid having inlet and outlet means;
   (c) a plurality of fluid flow channels positioned within said chamber means so that said body fluid flows therebetween;
   (d) fixed on said fluid flow channels a non-radiation grafted biospecific polymer comprising a biocompatible polymer support, a spacer covalently bonded to said biocompatible polymer support and a biological or biologicals covalently bonded to said spacer such that said biological or biologicals extend away from the surface of said polymer support, which biospecific polymer will chemically bond at least one pathological effector carried by said body fluid to remove said pathological effector therefrom; and (e) means for returning said body fluid to said patient.

14. The device as recited in claim 13 wherein the biocompatible polymer support comprises a terpolymer of glycidyl methacrylate, N-vinyl pyrrolidone and hydroxyethyl methacrylate.

15. A therapeutic method for the treatment of a body fluid which comprises:

(a) withdrawing said body fluid from a patient;
(b) admitting said body fluid into a chamber means;
(c) contacting said body fluid within said chamber with a non-radiation grafted biospecific polymer comprising a biocompatible polymer support, a spacer covalently bonded to said biocompatible polymer support, and a biological or biologicals covalently bonded to said spacer such that the biological or biologicals extend away from the surface of said polymer support, which biospecific polymer will chemically bond at least one pathological effector carried by said body fluid to said biospecific polymer to remove said pathological effector from said body fluid; and
(d) removing said body fluid from said chamber and returning said body fluid to said patient.

16. The therapeutic method as recited in claim 15 wherein the withdrawing and returning steps are continuously performed.

17. The therapeutic method as recited in claim 15 wherein the body fluid to be treated is selected from the group consisting of blood, whole blood, blood plasma, and cerebrospinal fluid.

18. The method recited in claim 15 wherein said pathological effector is RF antigen.

19. The method recited in claim 15 wherein said pathological effector is RF antibody.

* * * * *